United States Patent [19]
Sugimura et al.

[11] Patent Number: 5,811,540
[45] Date of Patent: Sep. 22, 1998

[54] 5-O-PYRIMIDYL-2,3-DIDEOXY-1-THIOFURANOSIDE DERIVATIVE, AND PRODUCTION METHOD AND USE THEREOF

[75] Inventors: Hideyuki Sugimura, Sagamihara; Keiko Sujino, Kawagoe, both of Japan

[73] Assignee: The Noguchi Institute, Tokyo, Japan

[21] Appl. No.: 367,320

[22] PCT Filed: Nov. 4, 1994

[86] PCT No.: PCT/JP94/01867

§ 371 Date: Jan. 20, 1996

§ 102(e) Date: Jan. 20, 1996

[87] PCT Pub. No.: WO95/12593

PCT Pub. Date: May 11, 1995

[30] Foreign Application Priority Data

Nov. 5, 1993 [JP] Japan .................................. 5-299070

[51] Int. Cl.[6] .................................................. C07H 19/06
[52] U.S. Cl. ........................ 536/28.2; 536/4.1; 536/22.1; 536/28.1; 536/28.53; 536/28.54; 536/28.55; 536/29.13; 536/29.2
[58] Field of Search ..................... 536/4.1, 22.1, 536/28.2, 28.1, 28.53, 28.54, 28.55, 29.13, 29.2

[56] References Cited

PUBLICATIONS

General Syntheses of 2',3'-Dideoxynucleosides and 2',3'-Didehydro-2',3'-dideoxynucleosides—C.K. Chu et al,—J. Org. Chem. 1989, 54, pp. 2217-2225.

Synthesis and Structure–Activity Relationship of 6-Substituted 2',3'-Dideoxypurine Nucleosides as Potential Anti--Human Immunodeficiency Virus Agents—Chung K. Chu et al,—J. Med. Chem. 1990, 33, pp. 1553-1561.

Facile Synthesis of Pyrrolo[2,3-d]Pyrimidine and Pyrrolo[3,2-c]Pyridine 2',3'-Dideoxyribonucleosides Via Nucleobase Anion Glycosylation with 2,3-Dideoxy-D-Glycero--Pentofuranosyl Chloride—Heterocycles, vol. 29, No. 11, 1989.

Facile, Highly Stereoselective Synthesis of 2',3'-Dideoxy- and 2',3'-dideoxy Nucleosides via a Furanoid Glycal Intermediate—Choung Un Un Kim et al,—Tetrahedron Letters, vol. 33, No. 39, pp. 5733-5737, 1992.

Stereocontrolled Synthesis of β–D–2'–Deoxyribonucleosides by Intramolecular Glycosylation—Keiko Sujino et al,—Chemistry Letters, 1993, pp. 1187–1190.

The Journal of Organic Chemistry—vol. 58, No. 4, Feb. 12, 1993.

*Primary Examiner*—James O. Wilson
*Attorney, Agent, or Firm*—Armstrong, Westerman, Hattori, McLeland & Naughton

[57] ABSTRACT

Disclosed is a 5-O-pyrimidyl-2,3-dideoxy-1-thio-D-furanoside derivative represented by the following formula (I) or an L-form isomer thereof:

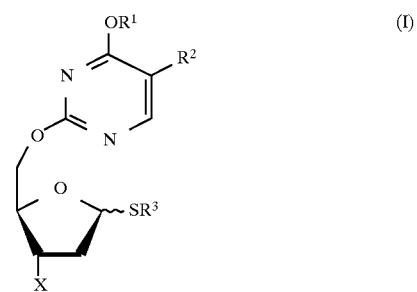

wherein X represents a hydrogen atom, a fluorine atom or an azido group; $R^1$ represents a $C_{1-4}$ alkyl group; $R^2$ represents a hydrogen atom, a methyl group or a fluorine atom or a trifluoromethyl group; $R^3$ represents a $C_{1-10}$ alkyl group or a $C_{6-15}$ aryl group which is unsubstituted or substituted with at least one substituent selected from the group consisting of a chlorine atom, a bromine atom, a methyl group, an ethyl group and a nitro group. When this derivative is reacted with a sulfonium ion-generating reagent to thereby effect an intramolecular N-glycosylation of the derivative, a β-2',3'-dideoxynucleoside derivative which is useful as a precursor of an antiviral agent, such as AZT, DDC or FLT, can be produced with an extremely high stereoselectivity for the β-anomer and in high yield while very little or none of the α-form isomer corresponding thereto is produced.

5 Claims, 8 Drawing Sheets

5-O-PYRIMIDYL-2,3-DIDEOXY-1-THIOFURANOSIDE DERIVATIVE, AND PRODUCTION METHOD AND USE THEREOF

BACKGROUND OF THE INVENTION

1. Technical Field

The present invention relates to a novel 5-O-pyrimidyl-2,3-dideoxy-1-thiofuranoside derivative, and a production method and a use thereof. More particularly, the present invention is concerned with a 5-O-pyrimidyl-2,3-dideoxy-1-thiofuranoside derivative useful as an intermediate for synthesizing a β-2',3'-dideoxynucleoside derivative which is known to exhibit an antiviral activity, a method for producing the same, and a method for stereos electively producing a β-2',3'-dideoxynucleoside derivative from the 5-O-pyrimidyl-2,3-dideoxy-1-thiofuranoside derivative. By the method of the present invention, a β-2',3'-dideoxynucleoside derivative can be easily produced in high yield without producing an α-anomer corresponding thereto. The β-2',3'-dideoxynucleoside derivative obtained by the method of the present invention is useful as a precursor of various antiviral agents, such as 3'-azido-3'-deoxythymidine (AZT), 2',3'-dideoxycytidine (DDC), and 3'-fluoro-3'-deoxythymidine (FLT), which are capable of suppressing the multiplication of human immunodeficiency virus (HIV). AZT and DDC have been widely used as a therapeutic reagent for AIDS.

2. Background Art

Conventional methods for synthesizing a β-2',3'-dideoxynucleoside derivative can be classified into two groups. In the method of the first group, a β-2',3'-dideoxynucleoside derivative is obtained by deoxidizing the hydroxyl group at each of the 2'- and 3'-positions of a natural or synthesized β-ribonucleoside (C. K. Chu et al., J. Org. Chem., vol. 54, p. 2217, 1989). In the method of the second group, a β-2',3'-dideoxynucleoside derivative is obtained by coupling a 2,3-dideoxysugar derivative with a nucleic acid base. With respect to examples of such a coupling method, reference can be made to a method in which a leaving group at the anomeric carbon atom position of a 2,3-dideoxysugar is eliminated using an activating agent (e.g., a Lewis acid) and then, a nucleic acid base is bonded to the anomeric carbon atom position (C. K. Chu et al., J. Med. Chem., vol. 33, p. 1553, 1990); a method in which a 1-chloro-2,3-dideoxysugar is reacted with a sodium salt or potassium salt of a nucleic acid base (F. Seela et al., Heterocycles, vol. 29, p. 2193, 1989); and a method in which an addition reaction of a nucleic acid base to a glycal is effected (C. U. Kim et al., Tetrahedron lett., vol. 33, p. 5733, 1992).

However, in the above-mentioned method of the first group, the starting material is expensive, and the deoxidization reaction requires a complicated procedure having a number of synthesizing steps involved therein. On the other hand, in the above-mentioned method of the second group, an undesirable α-anomer is formed simultaneously with the formation of the desired β-anomer, leading to a lowering in yield of the desired β-anomer. Further, in this method, the α-anomer and the β-anomer are usually formed in mixture thereof. It is difficult to separate the β-anomer from the α-anomer by conventional purification processes and, therefore, for obtaining the desired β-anomer in pure form, it is necessary to repeat the separation procedure many times, which is very cumbersome. In the method in which a 1-chloro-2,3-dideoxysugar is used in the coupling reaction, this starting sugar itself is unstable, so that the use of such a starting material is disadvantageous in preparation and handling thereof. The method in which the addition reaction of a base to a glycal is effected is also disadvantageous in that the substituent at the 2'-position of the resultant nucleoside, which substituent is formed by the addition reaction, must be finally removed. Thus, any of the conventional methods for synthesizing a β-2',3'-dideoxynucleoside derivative is not satisfactory for practice on a commercial scale.

DISCLOSURE OF THE INVENTION

With a view toward developing a method for the efficient synthesis of a 2',3'-dideoxynucleoside derivative with a high selectivity for the β-anomer, the present inventors have made extensive and intensive studies. As a result, they have surprisingly found that when a novel 5-O-pyrimidyl-2,3-dideoxy-l-thio-D-furanoside derivative represented by formula (I), or an L-form isomer thereof:

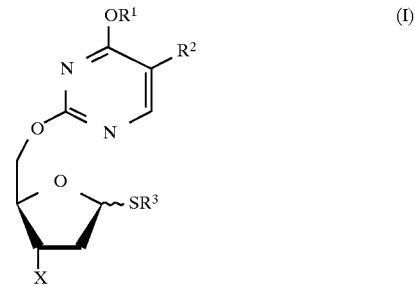

wherein X represents a hydrogen atom, a fluorine atom or an azido group; $R^1$ represents a $C_1$–$C_4$ alkyl group; $R^2$ represents a hydrogen atom, a methyl group, a fluorine atom or a trifluoromethyl group; and $R^3$ represents a $C_1$–$C_{10}$ alkyl group or a $C_6$–$C_{15}$ aryl group which is unsubstituted or substituted with at least one substituent selected from the group consisting of a chlorine atom, a bromine atom, a methyl group, an ethyl group and a nitro group, is reacted with a sulfonium ion-generating reagent to thereby effect an intramolecular N-glycosylation reaction of the 5-O-pyrimidyl-2,3-dideoxy-1-thio-D-furanoside derivative or an L-form isomer thereof, and the resultant reaction product is treated in situ with an aqueous alkaline solution, a β-2',3'-dideoxynucleoside derivative can be easily produced in high yield and with a stereoselectivity as high as 100% for the desired β-anomer. The present invention has been completed, based on the above novel findings.

Accordingly, it is an object of the present invention to provide a novel 5-O-pyrimidyl-2,3-dideoxy-1-thiofuranoside derivative useful as an intermediate for synthesizing a β-2',3'-dideoxynucleoside derivative which is useful as a precursor of an excellent antiviral agent, with an extremely high stereoselectivity for the β-anomer.

It is another object of the present invention to provide a method for producing the above-mentioned novel 5-O-pyrimidyl-2,3-dideoxy-1-thiofuranoside derivative in high yield.

It is a further object of the present invention to provide a method for efficiently producing a β-2',3'-dideoxynucleoside derivative useful as a precursor of an excellent antiviral agent from the above-mentioned novel 5-O-pyrimidyl-2,3-dideoxy-1-thiofuranoside derivative in high yield and with an extremely high stereoselectivity for the β-anomer.

The foregoing and other objects, features and advantages of the present invention will be apparent from the following detailed description and appended claims taken in connection with the accompanying drawings.

DETAILED DESCRIPTION OF THE INVENTION

Figure 1:
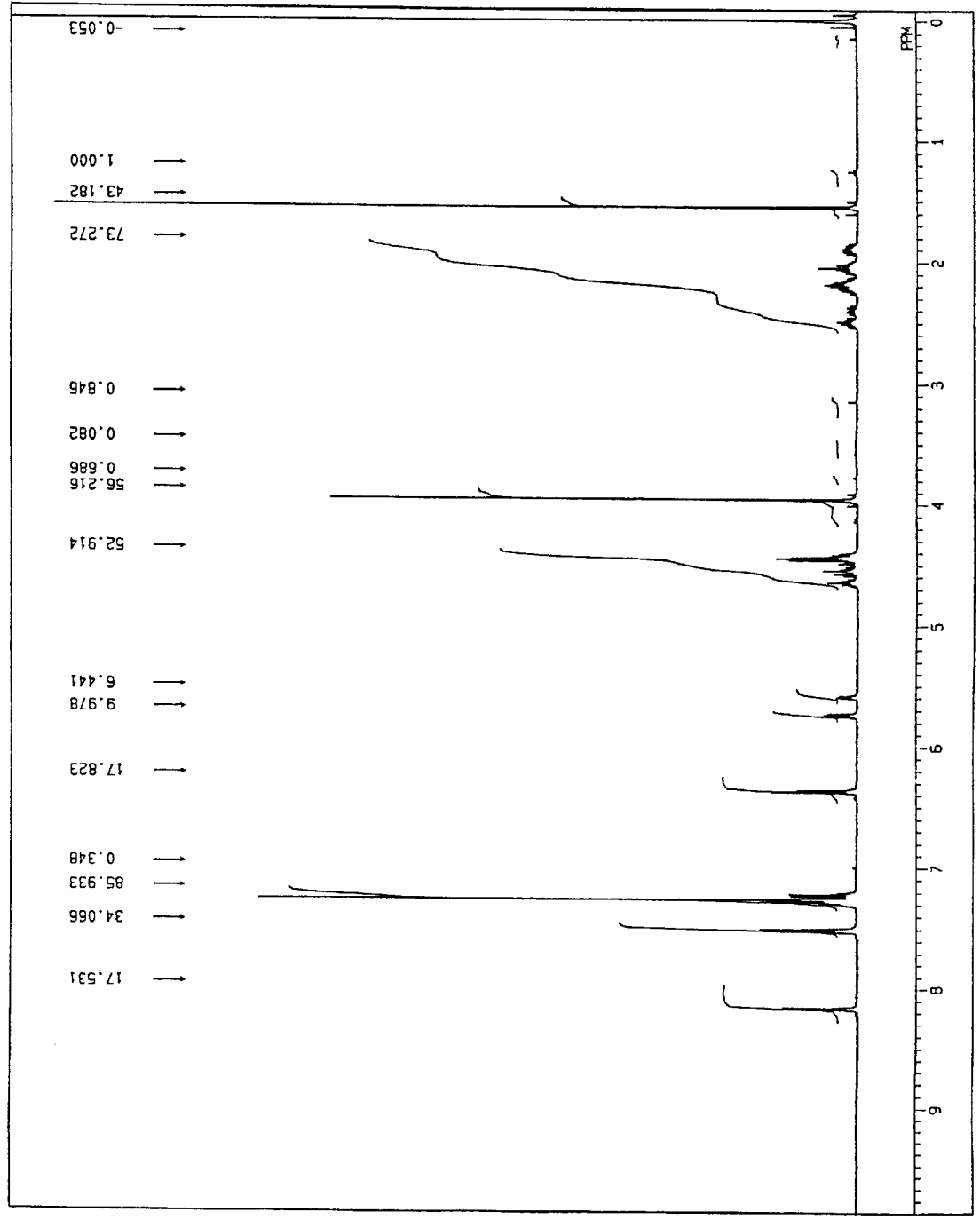
FIG. 1 is a chart showing the $^1$H NMR spectrum of the 5-O-pyrimidyl-2,3-dideoxy-1-thio-D-furanoside derivative obtained in Example 1.

In one aspect of the present invention, there is provided a 5-O-pyrimidyl-2,3-dideoxy-1-thio-D-furanoside derivative represented by formula (I), or an L-form isomer thereof:

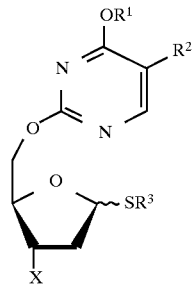

(I)

wherein X represents a hydrogen atom, a fluorine atom or an azido group; $R^1$ represents a $C_1$–$C_4$ alkyl group; $R^2$ represents a hydrogen atom, a methyl group, a fluorine atom or a trifluoromethyl group; and $R^3$ represents a $C_1$–$C_{10}$ alkyl group or a $C_6$–$C_{15}$ aryl group which is unsubstituted or substituted with at least one substituent selected from the group consisting of a chlorine atom, a bromine atom, a methyl group, an ethyl group and a nitro group.

The novel 5-O-pyrimidyl-2,3-dideoxy-1-thio-D-furanoside derivative of the present invention or an L-form isomer thereof can be produced by the method illustrated by way of the following reaction scheme, wherein the furanoside derivatives are shown in D-form.

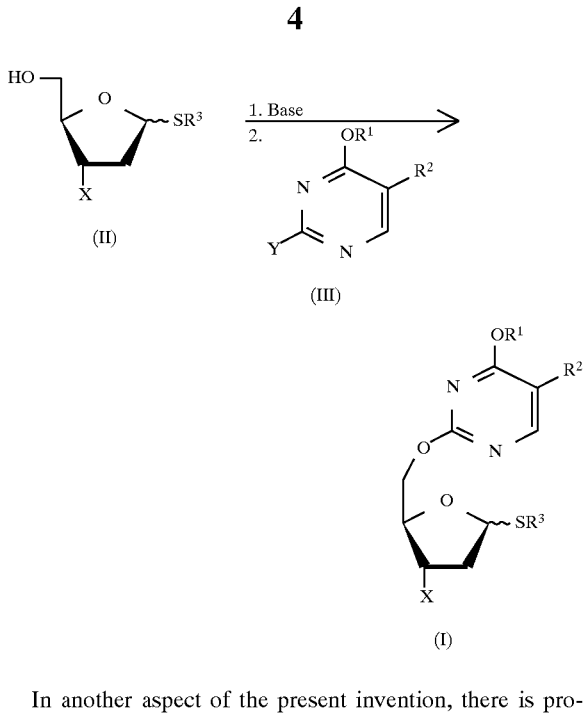

In another aspect of the present invention, there is provided a method for producing a 5-O-pyrimidyl-2,3-dideoxy-1-thiofuranoside derivative represented by formula (I), or an L-form isomer thereof:

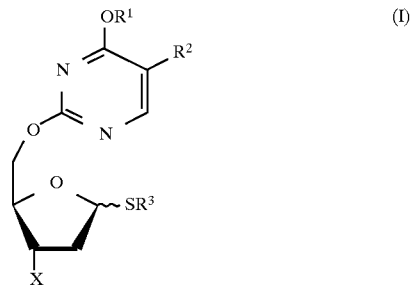

(I)

wherein X represents a hydrogen atom, a fluorine atom or an azido group; $R^1$ represents a $C_1$–$C_4$ alkyl group; $R^2$ represents a hydrogen atom, a methyl group, a fluorine atom or a trifluoromethyl group; and $R^3$ represents a $C_1$–$C_{10}$ alkyl group or a $C_6$–$C_{15}$ aryl group which is unsubstituted or substituted with at least one substituent selected from the group consisting of a chlorine atom, a bromine atom, a methyl group, an ethyl group and a nitro group, which comprises the steps of:

(1) reacting a 2,3-dideoxy-1-thio-D-furanoside derivative represented by formula (II), or an L-form isomer thereof:

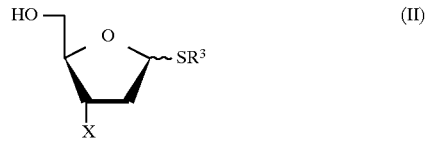

(II)

wherein X represents a hydrogen atom, a fluorine atom or an azido group; and $R^3$ represents a $C_1$–$C_{10}$ alkyl group or a $C_6$–$C_{15}$ aryl group which is unsubstituted or substituted with a chlorine atom, a bromine atom, a methyl group, an ethyl group or a nitro group, with a base selected from the group consisting of sodium hydride and potassium hydride; and (2) reacting in situ the resultant reaction product with a pyrimidine derivative represented by formula (III):

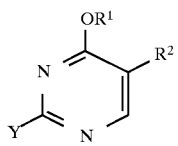

wherein Y represents a chlorine atom, a bromine atom or a methylthio group; $R^1$ represents a $C_{1-4}$ alkyl group; and $R^2$ represents a hydrogen atom, a methyl group, a fluorine atom or a trifluoromethyl group.

Hereinafter, a 5-O-pyrimidyl-2,3-dideoxy-1-thio-D-furanoside derivative represented by formula (I) or an L-form isomer thereof, a 2,3-dideoxy-1-thio-D-furanoside derivative represented by formula (II) or an L-form isomer thereof, and a pyrimidine derivative represented by formula (III) are frequently referred to simply as "5-O-pyrimidyl-2, 3-dideoxy-1-thiofuranoside derivative (I)", "2,3-dideoxy-1-thiofuranoside derivative (II)" and "pyrimidine derivative (III)", respectively.

With respect to the 2,3-dideoxy-1-thiofuranoside derivative (II) to be used as a starting material in the above-mentioned method of the present invention, X represents a hydrogen atom, a fluorine atom or an azido group, and $R^3$ represents a $C_1$–$C_{10}$ alkyl group or a $C_6$–$C_{15}$ aryl group which is unsubstituted or substituted with at least one substituent selected from the group consisting of a chlorine atom, a bromine atom, a methyl group, an ethyl group and a nitro group. As $R^3$, a phenyl group is preferably used.

With respect to the pyrimidine derivative (III), Y represents a chlorine atom, a bromine atom or a methyl-thio group, $R^1$ represents a $C_1$–$C_4$ alkyl group, and $R^2$ represents a hydrogen atom, a methyl group, a fluorine atom or a trifluoromethyl group. It is preferred to employ a chlorine atom as Y, a methyl group as $R^1$, and a hydrogen atom, fluorine atom or a methyl group as $R^2$.

The 5-O-pyrimidyl-2,3-dideoxy-1-thiofuranoside derivative (I) of the present invention is produced as follows. To a solution of a 2,3-dideoxy-1-thiofuranoside derivative (II) as the starting material in an aprotic solvent (e.g., dimethylformamide) is added 1 to 5 mol, preferably 1.5 to 3 mol of a base selected from the group consisting of sodium hydride and potassium hydride, per mol of the 2,3-dideoxy-1-thiofuranoside derivative (II), and the reaction is conducted at 0 ° to 50° C., preferably 15° to 25° C., for 0.5 to 5 hours, preferably 1 to 2 hours. Then, 1 to 5 mol, preferably 1.5 to 3 mol of a pyrimidine derivative (III) is added to the reaction mixture, per mol of the 2,3-dideoxy-1-thiofuranoside (II), and the reaction is allowed to proceed, to thereby produce a 5-O-pyrimidyl-2,3-dideoxy-1-thiofuranoside derivative (I). In this instance, it is preferred that the pyrimidine derivative (III) be added to the reaction mixture at −50° to 10° C. and the reaction temperature be gradually elevated to 15° to 40° C. to advance the reaction for 5 to 18 hours. The aprotic solvent is used in an amount of 1 to 10 liters, preferably 3 to 7 liters, per mol of the 2,3-dideoxy-1-thiofuranoside derivative (II).

By the use of the above-obtained 5-O-pyrimidyl-2, 3-dideoxy-1-thiofuranoside derivative (I) of the present invention, a β-2',3'-dideoxynucleoside derivative which is useful as a precursor of an antiviral agent can be produced in high yield and with an extremely high stereoselectivity for the β-anomer, and very little or no α-anomer corresponding thereto is produced. The method for producing a β-2',3'-dideoxynucleoside derivative can be illustrated by the following reaction scheme:

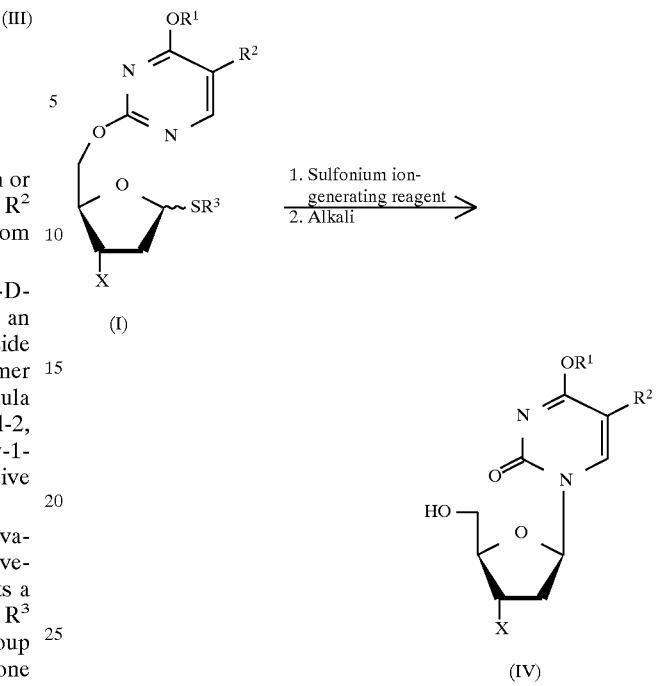

That is, in a further aspect of the present invention, there is provided a method for producing a β-2', 3'-dideoxynucleoside derivative represented by formula (IV), or an L-form isomer thereof:

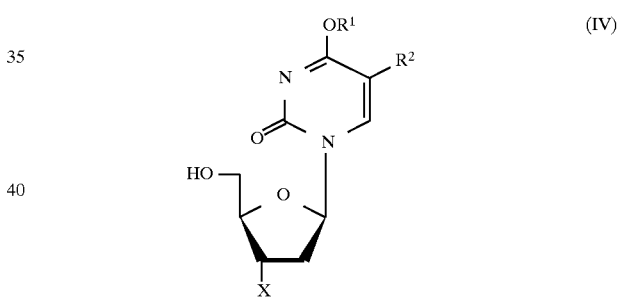

wherein X represents a hydrogen atom, a fluorine atom or an azido group; $R^1$ represents a $C_1$–$C_4$ alkyl group; and $R^2$ represents a hydrogen atom, a methyl group, a fluorine atom or a trifluoromethyl group, which comprises the steps of:

(1) reacting a 5-O-pyrimidyl-2,3-dideoxy-1-thio-D-furanoside derivative as defined above or an L-form isomer thereof with a sulfonium ion-generating reagent to thereby effect an intramolecular N-glycosylation reaction of the 5-O-pyrimidyl-2,3-dideoxy-1-thio-D-furanoside derivative or the L-form isomer thereof; and (2) treating in situ the resultant reaction product with an aqueous alkaline solution.

Hereinafter, a β-2',3'-dideoxynucleoside derivative represented by formula (IV) or an L-form isomer thereof is frequently referred to simply as "β-2',3'-dideoxynucleoside derivative (IV)".

In the above method, a 5-O-pyrimidyl-2,3-dideoxy-1-thiofuranoside derivative (I) is reacted with a sulfonium ion-generating reagent to effect an intramolecular N-glycosylation reaction of the 5-O-pyrimidyl-2, 3-dideoxy-1-thiofuranoside derivative (I), thereby converting the 5-O-pyrimidyl-2,3-dideoxy-1-thiofuranoside derivative (I) to a β-2',3'-dideoxynucleoside derivative (IV). Examples of sulfonium ion-generating reagents to be used in the method of the present invention include a dimethyl (methylthio)sulfonium salt selected from the group consisting of a dimethyl(methylthio)sulfonium tetrafluoroborate and a dimethyl(methylthio)sulfonium triflate, and a system which is comprised of a sulfenyl chloride and an appropriate silver salt, such as silver perchlorate or silver trifluoromethanesulfonate, and which can generate a sulfonium ion. The sulfonium ion-generating reagent can be used in an amount of 1 to 2 mol, preferably 1.1 to 1.3 mol, per mol of the 5-O-pyrimidyl-2,3-dideoxy1-thiofuranoside derivative (I).

The N-glycosylation reaction can be performed in the following manner. To a solution of a 5-O-pyrimidyl-2, 3-dideoxy-1-thiofuranoside derivative (I) in an aprotic solvent (such as an acetonitrile, dichloromethane or dimethylformamide) is added a sulfonium ion-generating reagent in the presence of Molecular Sieves 4A (manufactured by KOKUSAN Chemical Works, Ltd., Japan) under the atmosphere of an inert gas, such as nitrogen or argon, and a reaction is allowed to proceed at −78° to 25° C., preferably −20° to 0° C., for 1 to 12 hours, preferably 5 to 7 hours. The aprotic solvent is used in an amount of 100 to 500 liters, preferably 200 to 300 liters, per mol of the 5-O-pyrimidyl-2,3-dideoxy-1-thiofuranoside derivative (I). Then, an aqueous alkaline solution is added to the resultant reaction mixture in an excess amount relative to the starting 5-O-pyrimidyl-2,3-dideoxy-1-thiofuranoside derivative (I), and the resultant mixture is stirred at −10° to 25° C., preferably 0° to 10° C., for 1 to 5 hours, preferably 2 to 3 hours, to thereby produce the desired β-2', 3'-dideoxynucleoside derivative (IV). As the aqueous alkaline solution, a 1N aqueous solution of sodium hydroxide, a saturated aqueous sodium carbonate solution or a saturated aqueous sodium hydrogencarbonate solution can be used. Of these, a 1N aqueous sodium hydroxide solution is preferably used.

The β-2',3'-dideoxynucleoside derivative obtained by the method of the present invention can be readily converted to a known antiviral agent, such as AZT, DDC or FLT by the treatment with an acid or ammonia.

BEST MODE FOR CARRYING OUT THE INVENTION

Hereinbelow, the present invention will be described in more detail with reference to the following Examples, but they should not be construed to be limiting the scope of the present invention.

In the following Examples, 2,3-dideoxy-1-thio-D-furanoside derivatives were employed to produce β-2', 3'-dideoxynucleoside derivatives. However, the L-form isomers thereof can also be employed to produce the corresponding L-form β-2',3'-dideoxynucleoside derivatives.

With respect to the compound obtained in each of Examples, NMR spectrum was obtained using an NMR spectrometer, EX-400 (manufactured by JEOL. Ltd., Japan).

EXAMPLE 1

Step 1: Production of phenyl 2,3-dideoxy-5-O-(4-methoxy-2-pyrimidyl)-1-thio-D-glycero-pentofuranoside To the phenyl 2,3-dideoxy-1-thio-D-glycero-pentofuranoside (465 mg, 2.21 mmol) was added dimethylformamide (10 ml) under an argon atmosphere and then, sodium hydride (50% oil, 230 mg) having been washed with hexane was added thereto. The resultant mixture was allowed to react at room temperature for 1 hour and cooled to 0° C. To the reaction mixture was added 2-chloro-4-methoxypyridine (519 mg) and a reaction was allowed to proceed for 3 hours. The resultant mixture was gradually heated to room temperature, so that a reaction is further allowed to proceed for 12 hours. After cooling the resultant mixture to 0° C., water and ether were added thereto to thereby extract the organic phase of the mixture with the ether. The thus obtained organic phase was dried over anhydrous magnesium sulfate and concentrated by evaporation of the ether under reduced pressure. The resultant concentrate was subjected to silica gel thin-layer chromatography (developing solvent; ether:hexane=1:2 to 3:1) to thereby obtain 631 mg of phenyl 2,3-dideoxy-5-O-(4-methoxy-2-pyrimidyl)-1-thio-D-glycero-pentofuranoside (yield: 90%). The structure of this compound was confirmed by $^1$H NMR. The $^1$H NMR spectrum is shown in FIG. 1, and the $^1$H NMR data is as follows:

$^1$H NMR (CDCl$_3$): δ=1.85–1.93 (m), 2.00–2.19 (m), 2.12–2.26 (m), 2.36–2.43 (m), 2.46–2.55 (m), 3.96 (s), 4.40–4.68 (m), 5.59 (dd, J=3.9, 6.8 Hz), 5.74 (dd, J=4.2, 7.2 Hz), 6.36 (d, J=5.9 Hz), 6.37 (d, J=5.9 Hz), 7.20–7.31 (m), 7.49–7.53 (m), 8.16 (d, J=5.4 Hz), 8.17 (d, J=5.9 Hz).

Figure 5:
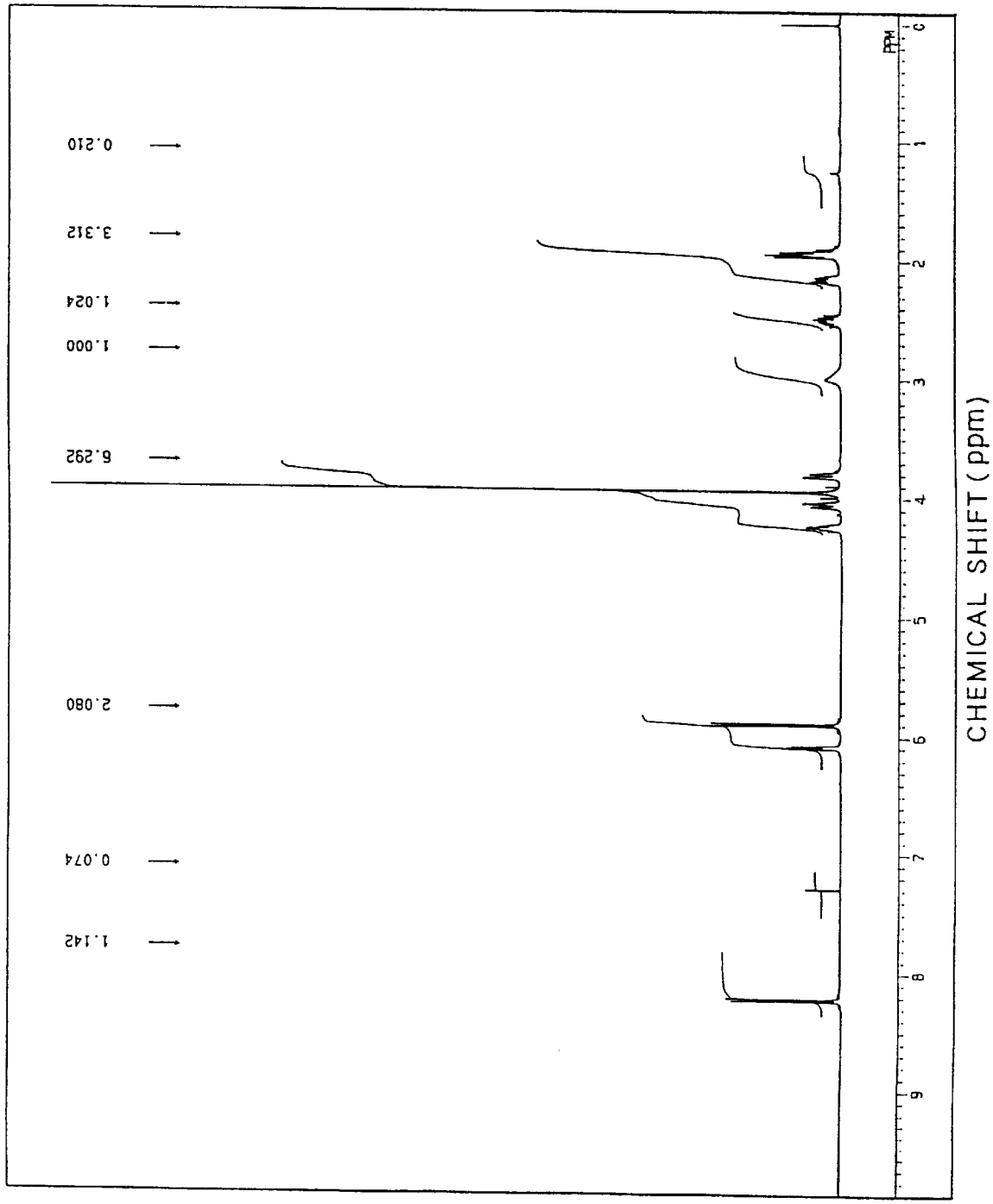
FIG. 5 is a chart showing the $^1$H NMR spectrum of the β-2',3'-dideoxynucleoside derivative obtained in Example 1.

Step 2: Production of 1-(2,3-dideoxy-β-D-glycero-pentofuranosyl)-4-methoxy-2-(1H)-pyrimidinone To the phenyl 2,3-dideoxy-5-O-(4-methoxy-2-pyrimidyl)-1-thio-D-glycero-pentofuranoside (α:β=1.4:1, 106.1 mg, 0.333 mmol) obtained in Step 1 above were added 83 ml of acetonitrile and 830 mg of Molecular Sieves 4A under an argon atmosphere. After 30 minutes, the resultant mixture was cooled to −20° C., and 74.1 mg of dimethyl(methylthio) sulfonium tetrafluoroborate (97%, 0.367 mmol) was added thereto. After 5 hours, an 1N aqueous sodium hydroxide solution (25 ml) was added to the mixture, and a reaction was allowed to proceed at 0° C. for 2.5 hours. The resultant reaction mixture was neutralized with a saturated aqueous solution of ammonium chloride and then, subjected to extraction of the organic phase with chloroform. The organic phase thus extracted was washed with a saturated aqueous sodium chloride solution, and the washed organic phase was dried over anhydrous magnesium sulfate and concentrated by evaporation of the chloroform under reduced pressure. The resultant concentrate was subjected to silica gel thin-layer chromatography (developing solvent: ethyl acetate) to thereby obtain 54.1 mg of 1-(2,3-dideoxy-β-D-glycero-pentofuranosil)-4-methoxy-2-(1H)-pyrimidinone (yield: 72%). The structure of this compound was confirmed by $^1$H NMR. The $^1$H NMR spectrum is shown in FIG. 5, and the $^1$H NMR data is as follows:

$^1$H NMR (CDCl$_3$): δ=1.95 (m, 2H), 2.14 (ddd, 1H, J=4.0, 7.2, 13.5 Hz), 2.49 (m, 1H), 2.99 (br, 1H), 3.80 (dd, 1H, J=3.7, 12.9 Hz), 3.94 (s, 3H), 4.05 (d, 1H, J=12.2 Hz), 4.23 (m, 1H), 5.89 (d, 1H, J=7.8 Hz), 6.08 (dd, 1H, J=3.2, 6.6 Hz), 8.22 (d, 1H, J=7.3 Hz).

In this step, no α-anomer corresponding to the above-obtained β-anomer was produced.

EXAMPLE 2

Figure 2:
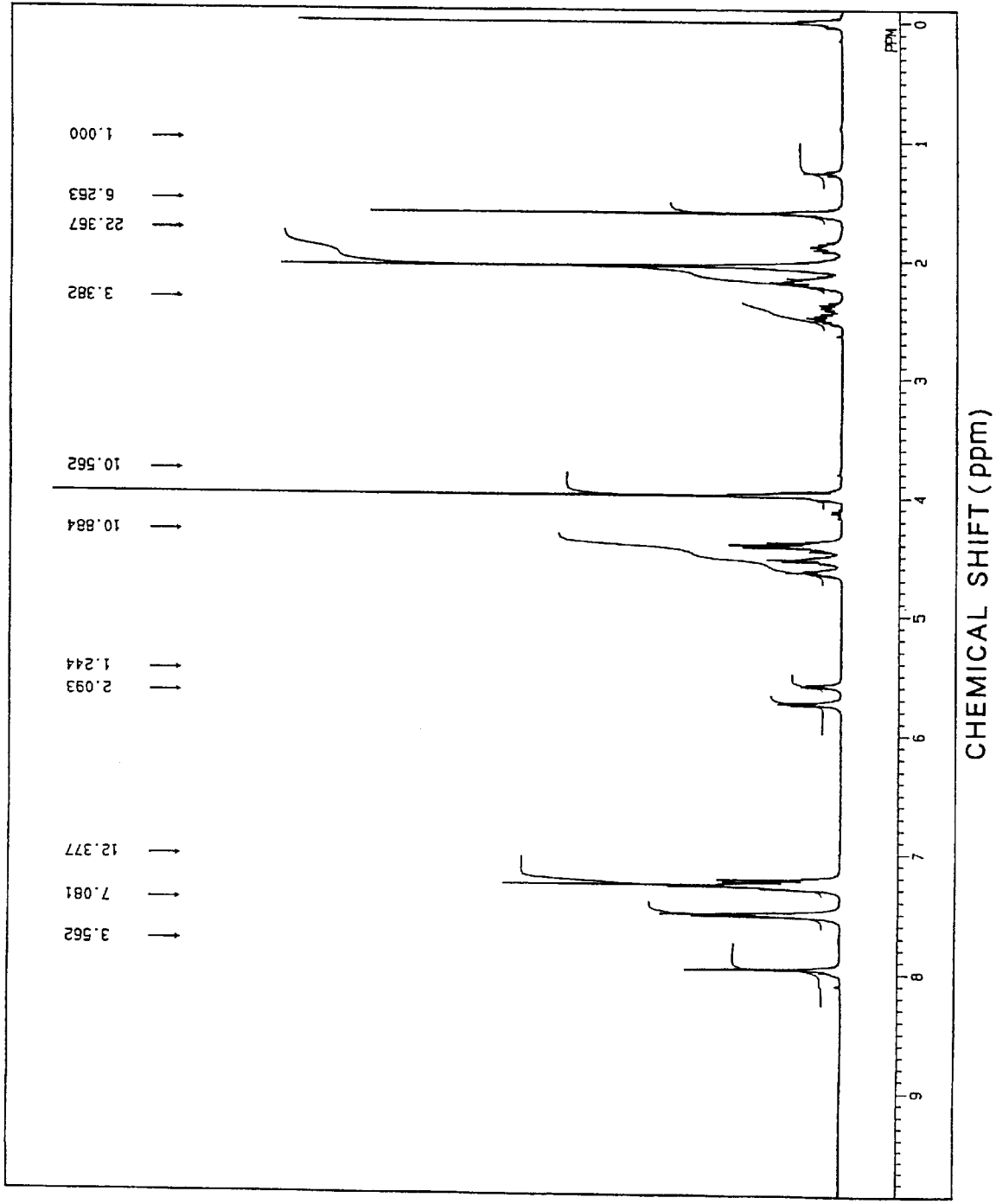
FIG. 2 is a chart showing the $^1$H NMR spectrum of the 5-O-pyrimidyl-2,3-dideoxy-1-thio-D-furanoside derivative obtained in Example 2.

Substantially the same procedure as in Step 1 of Example 1 was repeated, except that 2-chloro-4-methoxy-5-methylpyrimidine was used instead of the 2-chloro-4-methoxypyrimidine used in Example 1, whereby phenyl 2,3-dideoxy-5-O-(4-methoxy-5-methyl-2-pyrimidyl)-1-thio-D-glycero-pentofuranoside was produced (yield: 83%). The structure of this compound was confirmed by $^1$H NMR. The $^1$H NMR spectrum is shown in FIG. 2, and the $^1$H NMR data is as follows:

$^1$H NMR (CDCl$_3$): δ=1.84–1.92 (m), 1.99–2.09 (m), 2.03 (s), 2,04 (s), 2.11–2.25 (m), 2.35–2.43 (m), 2.45–2.54 (m), 3.98 (s), 4.24–4.68 (m), 5.59 (dd, J=3.9, 6.8 Hz), 5.74 (dd, J=4.2, 7.1 Hz), 7.20–7.30 (m), 7.50–7.52 (m), 7.96 (s).

Figure 6:
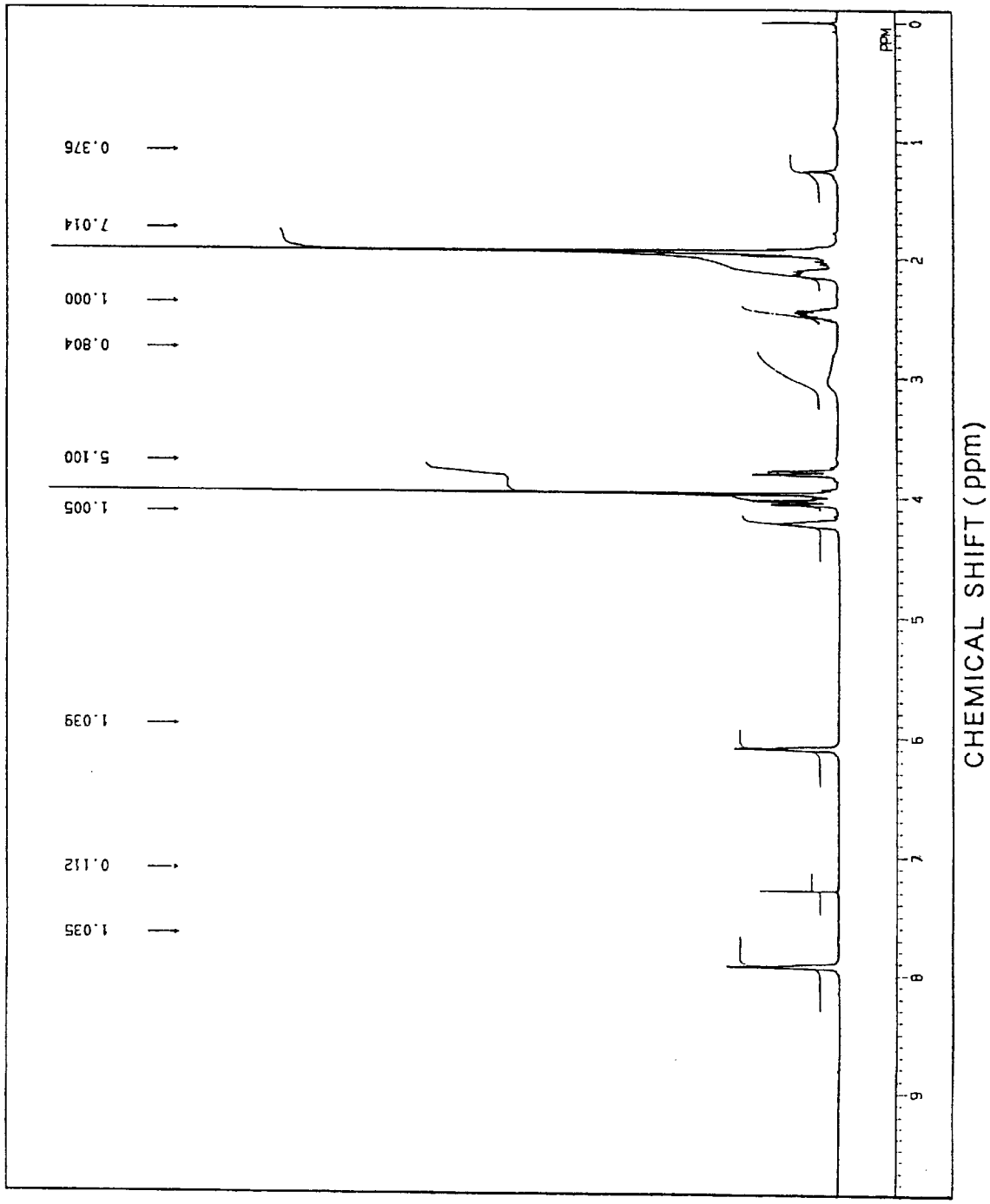
FIG. 6 is a chart showing the $^1$H NMR spectrum of the β-2',3'-dideoxynucleoside derivative obtained in Example 2.

Subsequently, substantially the same procedure as in Step 2 of Example 1 was repeated except that phenyl 2,3-dideoxy-5-O-(4-methoxy-5-methyl-2-pyrimidyl)-1-thio-D-glycero-pentofuranoside obtained above was used instead of the phenyl 2,3-dideoxy-5-O-(4-methoxy-2-pyrimidyl)-1-thio-D-glycero-pentofuranoside, to thereby produce 1-(2,3-dideoxy-β-D-glycero-pentofuranosyl)-4-methoxy-5-methyl-2-(1H)-pyrimidinone (yield: 79%). The structure of this compound was confirmed by $^1$H NMR. The $^1$H NMR spectrum is shown in FIG. 6, and the $^1$H NMR data is as follows:
$^1$H NMR (CDCl$_3$): δ=1.93 (d, 3H, J=1.95 Hz), 1.95 (m, 2H), 2.12 (m, 1H), 2.48 (m, 1H), 3.02(br, 1H), 3.79 (dd, 1H, J=3.9, 11.7 Hz), 3.97 (d, 3H, J=3.4 Hz), 4.04 (d, 1H, J=11.7 Hz), 4.21 (ddd, 1H, J=3.9, 7.3, 10.3 Hz), 6.09 (dt, 1H, J=2.9, 2.9, 6.4 Hz), 7.93 (s, 1H).

In this step, no α-anomer corresponding to the above-obtained β-anomer was produced.

EXAMPLE 3

Figure 3:
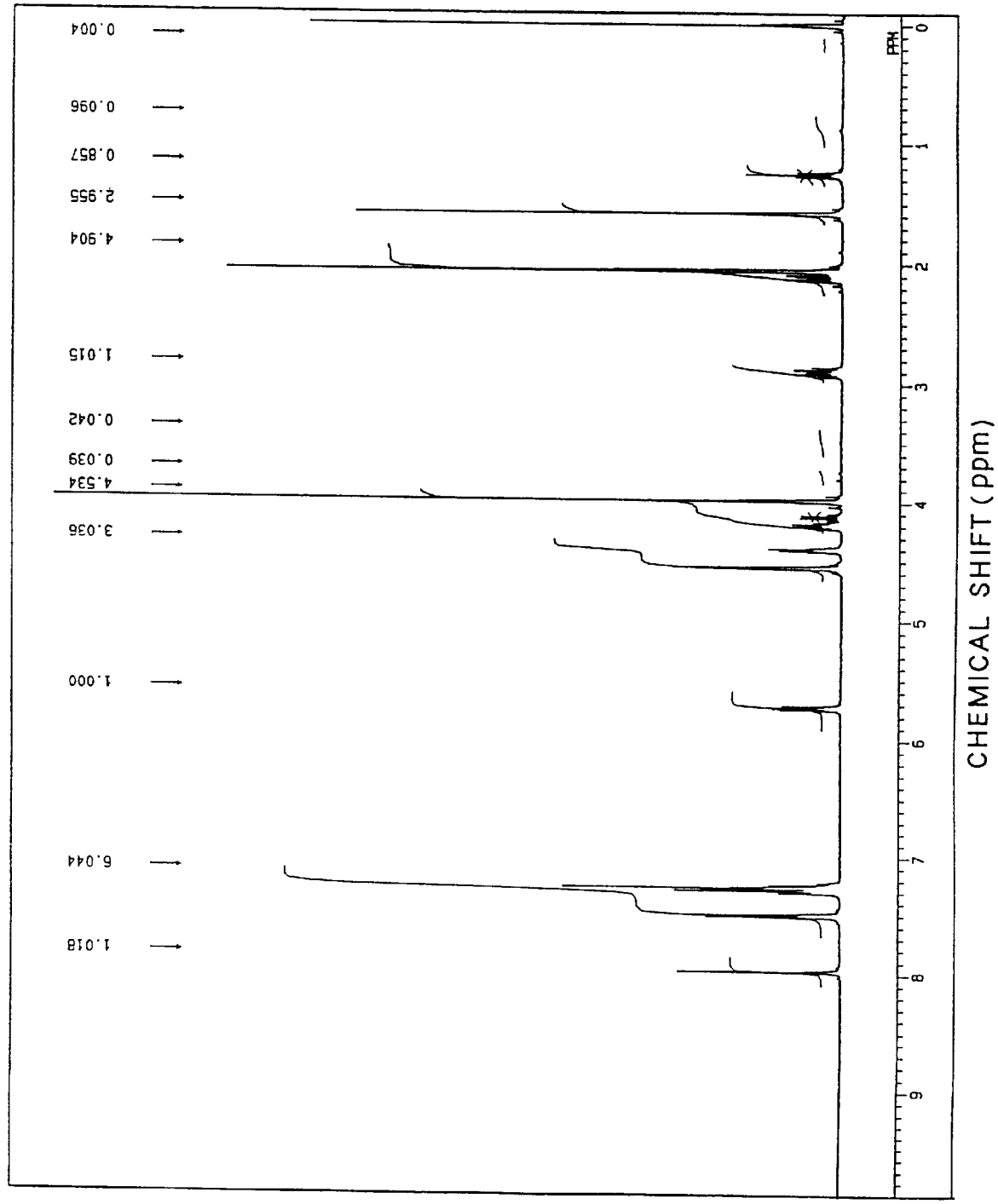
FIG. 3 is a chart showing the $^1$H NMR spectrum of the 5-O-pyrimidyl-1-2,3-dideoxy-1-thio-D-furanoside derivative obtained in Example 3.

Substantially the same procedure as in Step 1 of Example 2 was repeated, except that phenyl 3-azido-2,3-dideoxy-1-thio-α-D-erythro-pentofuranoside was used instead of the phenyl 2,3-dideoxy-1-thio-D-glycero-pentofuranoside, to thereby produce phenyl 3-azido-2,3-dideoxy-5-O-(4-methoxy-5-methyl-2-pyrimidyl)-1-thio-α-D-erythro-pentofuranoside (yield: 81%). The structure of this compound was confirmed by $^1$H NMR. The $^1$H NMR spectrum is shown in FIG. 3, and the $^1$H NMR data is as follows:
$^1$H NMR (CDCl$_3$): δ=2.06 (s, 3H), 2.11 (dt, 1H, J=5.1, 14.2 Hz), 2.90 (dt, 1H, J=8.1, 14.2 Hz), 3.99 (s, 3H), 4.19 (dt, 1H, J=6.0, 8.8 Hz), 4.40 (dt, 1H, J=3.5, 7.1 Hz), 4.53 (dd, 1H, J=3.9, 12.2 Hz), 4.57 (dd, 1H, J=3.9, 11.7 Hz), 5.73 (dd, 1H, J=4.9, 7.3 Hz), 7.24–7.31 (m, 3H), 7.49–7.51 (m, 2H), 7.98 (s, 1H).

Figure 7:
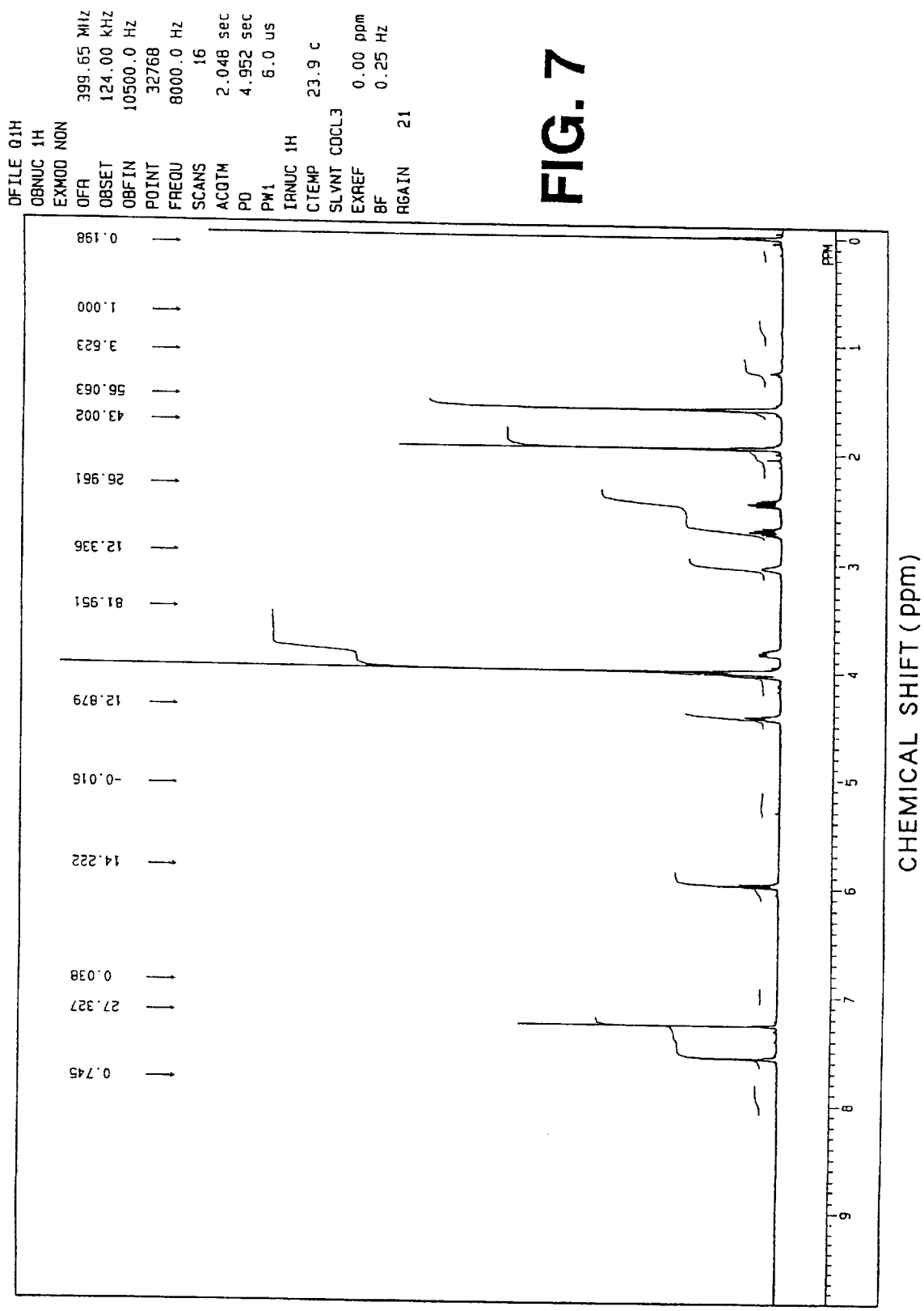
FIG. 7 is a chart showing the $^1$H NMR spectrum of the β2',3'-dideoxynucleoside derivative obtained in Example 3.

Subsequently, substantially the same procedure as in Step 2 of Example 2 was repeated except that phenyl 3-azido-2,3-dideoxy-5-O-(4-methoxy-5-methyl-2-pyrimidyl)-1-thio-α-D-erythro-pentofuranoside obtained above was used instead of the phenyl 2,3-dideoxy-5-O-(4-methoxy-5-methyl-2-pyrimidyl)-1-thio-D-glycero-pentofuranoside, to thereby produce 1-(3-azido-2,3-dideoxy-β-D-erythro-pentofuranosyl)-4-methoxy-5-methyl-2(1H)-pyrimidinone (yield: 84%). The structure of this compound was confirmed by $^1$H NMR. The $^1$H NMR spectrum is shown in FIG. 7, and the $^1$H NMR data is as follows:
$^1$H NMR (CDCl$_3$): δ=1.95 (d, 3H, J=0.98 Hz), 2.45 (ddd, 1H, J=5.2, 6.5, 13.8 Hz), 2.71 (dt, 1H, J=6.8, 6.8, 13.7 Hz), 3.04 (br, 1H), 3.82 (m, 1H), 3.99 (s, 3H), 3.99–4.04 (m, 2H), 4.42 (dd, 1H, J=2.0, 5.4 Hz), 5.98 (t, 1H, J=6.4 Hz), 7.26 (s, 1H).

In this step, no α-anomer corresponding to the above-obtained β-anomer was produced.

EXAMPLE 4

Figure 4:
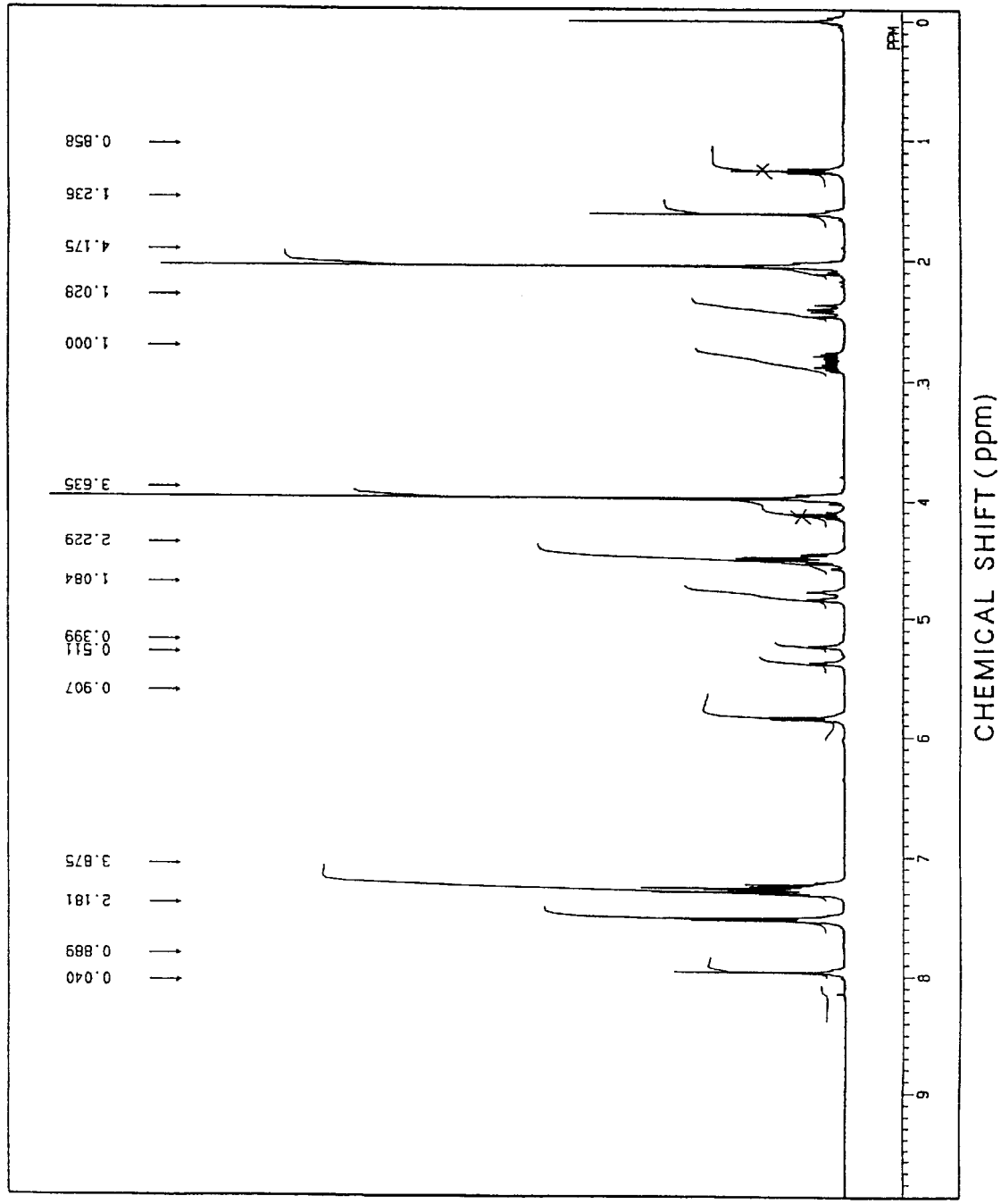
FIG. 4 is a chart showing the $^1$H NMR spectrum of the 5-O-pyrimidyl-2,3-dideoxy-1-thio-D-furanoside derivative obtained in Example 4.

Substantially the same procedure as Step 1 of Example 2 was repeated, except that phenyl 2,3-dideoxy-3-fluoro-1-thio-α-D-erythro-pentofuranoside was used instead of the phenyl 2,3-dideoxy-1-thio-D-glycero-pentofuranoside, to thereby produce phenyl 2,3-dideoxy-3-fluoro-5-O-(4-methoxy-5-methyl-2-pyrimidyl)-1-thio-α-D-erythro-pentofuranoside (yield: 81%). The structure of this compound was confirmed by $^1$H NMR. The $^1$H NMR spectrum is shown in FIG. 4, and the $^1$H NMR data is as follows:
$^1$H NMR (CDCl$_3$): δ=2.05 (s, 3H), 2.42 (dd, 1H, J=14.9, 24.2 Hz), 2.83 (dddd, J=6.4, 7.8, 14.7, 34.7 Hz), 3.98 (s, 3H), 4.46 (dd, 1H, J=4.6, 12.0 Hz), 4.52 (dd, 1H, J=3.9, 11.7 Hz), 4.81 (ddd, 1H, J=3.9, 6.3, 24.4 Hz), 5.31 (dd, 1H, J=6.4, 55.7 Hz), 5.84 (dd, 1H, J=2.2, 8.1 Hz), 7.19–7.31 (m, 3H) 7.43–7.51 (m, 2H), 7.96 (s, 1H).

Figure 8:
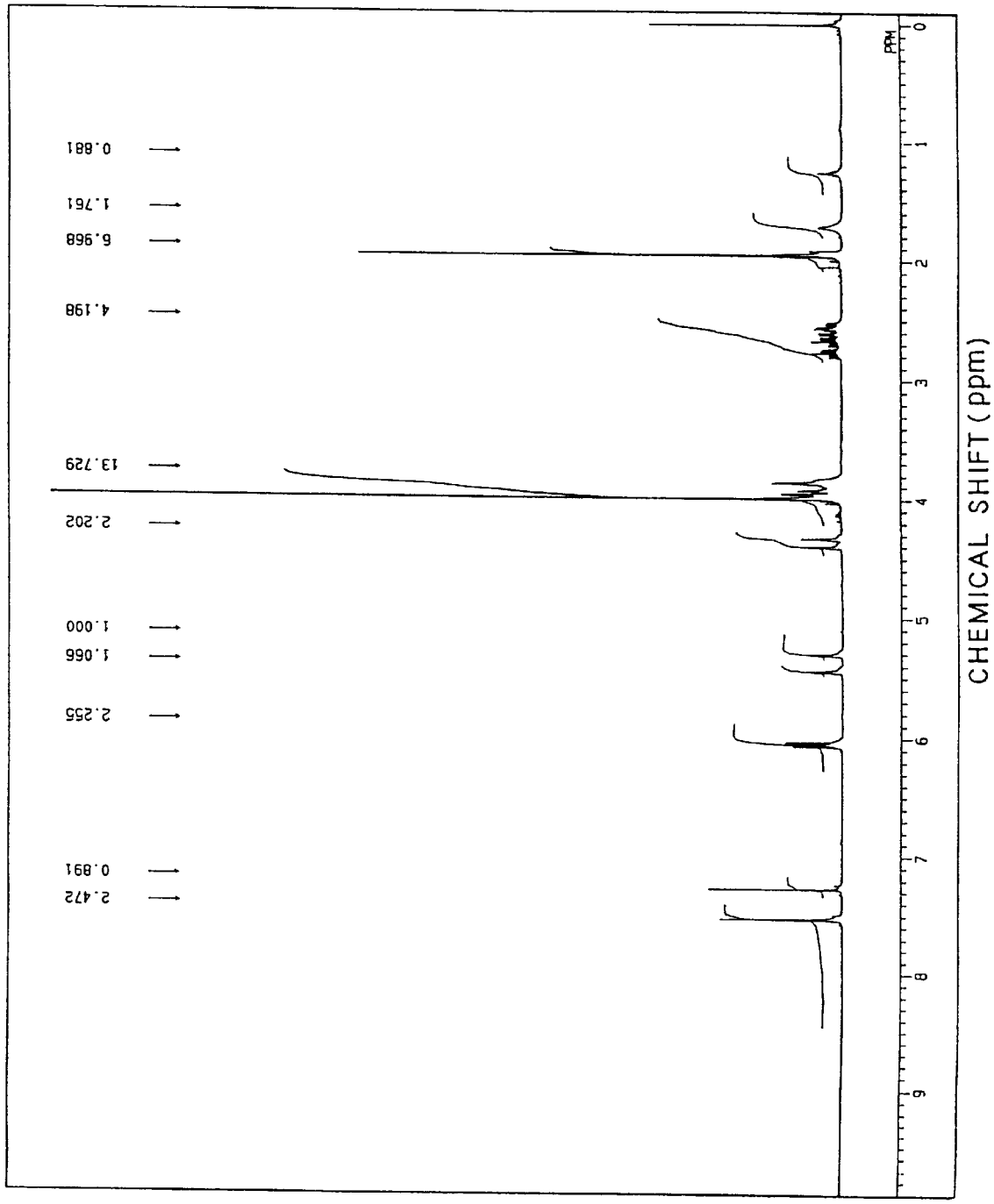
FIG. 8 is a chart showing the $^1$H NMR spectrum of the β-2',3'-dideoxynucleoside derivative obtained in Example 4.

Subsequently, substantially the same procedure as in Step 2 of Example 2 was repeated except that phenyl 2,3-dideoxy-3-fluoro-5-O-(4-methoxy-5-methyl-2-pyrimidyl)-1-thio-α-D-erythro-pentofuranoside obtained above was used instead of the phenyl 2,3-dideoxy-5-O-(4-methoxy-5-methyl-2-pyrimidyl)-1-thio-D-glycero-pentofuranoside, to thereby produce 1-(2,3-dideoxy-3-fluoro-β-D-erythro-pentofuranosyl)-4-methoxy-5-methyl-2(1H)-pyrimidinone (yield: 86%). The structure of this compound was also confirmed by $^1$H NMR. The $^1$H NMR spectrum is shown in FIG. 8, and the $^1$H NMR data is as follows:
$^1$H NMR (CDCl$_3$): δ=1.96 (d, 3H, J=0.98 Hz), 2.56 (ddd, 1H, J=5.9, 14.2, 21.0 Hz), 2.72 (dddd, 1H, J=4.9, 8.8, 14.2, 39.0 Hz), 3.85 (br, 2H), 3.97 (d, 1H, J =11.2 Hz), 3.99 (s, 3H), 4.36 (d, 1H, J=27.8 Hz), 5.37 (dd, 1H, J=4.9, 54.2 Hz), 6.05 (dd, 1H, J=5.9, 8.8 Hz), 7.52 (d, 1H, J=0.98 Hz).

In this step, no α-anomer corresponding to the above-obtained β-anomer was produced.

INDUSTRIAL APPLICABILITY

When the 5-O-pyrimidyl-2,3-dideoxy-1-thio-D-furanoside derivative represented by formula (I) of the present invention or an L-form isomer thereof is reacted with a sulfonium ion-generating reagent to thereby effect an intramolecular N-glycosylation reaction of the derivative (I), a β-2',3'-dideoxynucleoside derivative can be produced with an extremely high stereoselectivity for the β-anomer and in high yield, and very little or no α-form isomer corresponding thereto is produced. The β-2',3'-dideoxynucleoside derivative produced can be readily converted to an antiviral agent, such as AZT, DDC or FLT, by the treatment with an acid or ammonia.

We claim:

1. A 5-O-pyrimidyl-2,3-dideoxy-1-thio-D-furanoside derivative represented by formula (I), or an L-form isomer thereof:

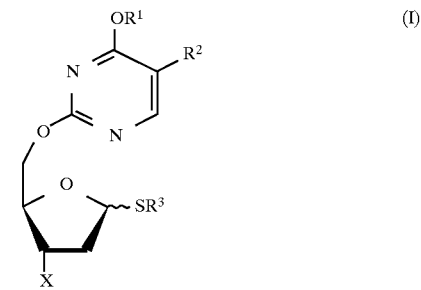

wherein X represents a hydrogen atom, a fluorine atom or an azido group; R$^1$ represents a C$_1$–C$_4$ alkyl group; R$^2$ represents a hydrogen atom, a methyl group, a fluorine atom or a trifluoromethyl group; and R$^3$ represents a C$_1$–C$_{10}$ alkyl group or a C$_6$–C$_{15}$ aryl group which is unsubstituted or substituted with at least one substituent selected from the group consisting of a chlorine atom, a bromine atom, a methyl group, an ethyl group and a nitro group.

2. The 5-O-pyrimidyl-2,3-dideoxy-1-thio-D-furanoside derivative or an L-form isomer thereof according to claim 1, wherein, in formula (I), X represents a hydrogen atom, $R^1$ represents a methyl group, $R^2$ represents a hydrogen atom, and $R^3$ represents a phenyl group.

3. The 5-O-pyrimidyl-2,3-dideoxy-1-thio-D-furanoside derivative or an L-form isomer thereof according to claim 1, wherein, in formula (I), X represents a hydrogen atom, $R^1$ represents a methyl group, $R^2$ represents a methyl group, and $R^3$ represents a phenyl group.

4. The 5-O-pyrimidyl-2,3-dideoxy-1-thio-D-furanoside derivative or an L-form isomer thereof according to claim 1, wherein, in formula (I), X represents an azido group, $R^1$ represents a methyl group, $R^2$ represents a methyl group, and $R^3$ represents a phenyl group.

5. The 5-O-pyrimidyl-2,3-dideoxy-1-thio-D-furanoside derivative or an L-form isomer thereof according to claim 1, wherein, in formula (I), X represents a fluorine atom, $R^1$ represents a methyl group, $R^2$ represents a methyl group, and $R^3$ represents a phenyl group.

* * * * *